US012562269B2

(12) United States Patent　　(10) Patent No.: US 12,562,269 B2
Berkes et al.　　　　　　　　　　　(45) Date of Patent: Feb. 24, 2026

(54) BODY-CONDITION-DEPENDENT STIMULATION WITH REAL-TIME COMMUNICATION BETWEEN AN ACTION MODULE AND A CAPTURE MODULE

(71) Applicant: NEUROCARE GROUP AG, Munich (DE)

(72) Inventors: Sebastian Berkes, Ilmenau (DE); Patrick Stein, Ilmenau (DE); Klaus Schellhorn, Ilmenau (DE)

(73) Assignee: NEUROCARE GROUP AG, Munich (DE)

( * ) Notice: Subject to any disclaimer, the term of this patent is extended or adjusted under 35 U.S.C. 154(b) by 506 days.

(21) Appl. No.: 18/007,651

(22) PCT Filed: Jun. 2, 2021

(86) PCT No.: PCT/EP2021/064780
§ 371 (c)(1),
(2) Date: Dec. 1, 2022

(87) PCT Pub. No.: WO2021/245129
PCT Pub. Date: Dec. 9, 2021

(65) Prior Publication Data
US 2023/0238128 A1　　Jul. 27, 2023

(30) Foreign Application Priority Data
Jun. 3, 2020　(DE) ......................... 102020114745.7

(51) Int. Cl.
*G16H 40/63*　　(2018.01)
*A61N 2/00*　　(2006.01)

(52) U.S. Cl.
CPC ............. *G16H 40/63* (2018.01); *A61N 2/006* (2013.01)

(58) Field of Classification Search
CPC ..... A61B 5/0004; A61B 5/0006; A61B 5/374; A61N 1/025; A61N 1/36025; A61N 2/006; G16H 40/63
See application file for complete search history.

(56) References Cited

U.S. PATENT DOCUMENTS 10,596,371 B1　3/2020　Lisy et al.
12,290,688 B1　5/2025　John
　　　　　　(Continued)

FOREIGN PATENT DOCUMENTS

WO　　2017099603 A1　6/2017
WO　　2018033591 A2　2/2018

OTHER PUBLICATIONS

Ciliberti, Davide, et al., "Falcon: a highly flexible open-source software for closed-loop neuroscience" Jun. 2017, pp. 1-16, Journal of Neural Engineering, XOP20318481.
(Continued)

*Primary Examiner* — George Manuel
(74) *Attorney, Agent, or Firm* — Armis IP Law, LLC

(57) ABSTRACT

The invention relates to a system for body-condition-dependent stimulation by means of function modules, e.g. an action module (2, D/A module) for stimulating tissue and a capture module (3, A/D module) for deriving/measuring bio data or bio signals, characterized in that the two modules communicate via a communication link (5) that meets hard or at least firm real-time requirements. The communication link (5) preferably comprises a real-time-capable bus to which the two modules are connected, above all an Ether-CAT bus.

13 Claims, 7 Drawing Sheets

(56)　　　　　References Cited

U.S. PATENT DOCUMENTS

| | | |
|---|---|---|
| 2011/0046687 A1 | 2/2011 | Naschberger |
| 2012/0016174 A1* | 1/2012 | De Taboada ............. A61N 5/04 |
| | | 607/3 |
| 2014/0330345 A1 | 11/2014 | John |
| 2018/0020941 A1 | 1/2018 | Hagedorn |
| 2020/0054888 A1 | 2/2020 | Etkin et al. |
| 2021/0124421 A1 | 4/2021 | Urbano |

OTHER PUBLICATIONS

Patel, Yogi, A., et al, "Hard real-time closed loop electrophysiology with the Real-Time eXperiment Interface (RTXI)", May 30, 2017, pp. 1-22, PLOS Computation Biology, XP055843227.
Roh, Tachwan, et al., "A Wearable Neuro-Feedback System With EEG-Based Mental Status Monitoring and Transcranial Electrical Stimulation", Dec. 2014, pp. 755-764, IEEE Transactions on Biomedical Circuits and Systems, vol. 8, No. 6, XP011570654.
Zitzewitz, Joachim Von, et al., "A neurorobotic platform for locomotor prosthetic development in rats and mice", published Feb. 9, 2016, pp. 1-15, XP020300685.
Japanese Office Action, JP 2022-574734, Feb. 27, 2025, pp. 8.
International Search Report, PCT/EP2021/064780, Sep. 3, 2021, pp. 1-5.
Jafarifarmand, Aysa, et al., "Real-time cardiac artifact removal from EEG using a hybrid approach", 2018, IEEE, pp. 1-5.
Rogasch, Nigel C., et al., "Analysing concurrent transcranial magnetic stimulation and electroencephalographic data: A review and introduction to the open-source TESA software" NeuroImage 147 (2017) pp. 934-951.
Search Report, 21 733 893.8, May 26, 2025, pp. 1-7.
Suresh, H.N., et al., "Removal of EMG and ECG artifacts from EEG based on real time recurrent learning algorithm", International Journal of Physical Sciences vol. 3 (5), May 2008, p. 120-125.
Gattinger, Norbert, et al. "flexTMS-A Novel Repetitive Transcranial Magnetic Stimulation Device With Freely Programmable Stimulus Currents", IEEE Transactions on Biomedical Engineering, vol. 59, No. 7, Jul. 2012, pp. 1-9.
Examination report, Intention to Grant, 21 733 893.8, Nov. 21, 2025, pp. 1-8.
Society Proceedings/Clinical Neurophysiology 124 (2013) e39-e187, p. 1.
Sorkhabi, et al. Deep-Brain Transcranial Stimulation: A Novel Approach for High 3-D Resolution, IEEE Access, vol. 5, Mar. 28, 2017, pp. 1-15.
Zrenner, Brigette, et al. Brain oscillation-synchronized stimulation of the left dorsolateral prefrontal cortex in depression using real-time EEG-triggered TMS, Brain Stimulation 13 (2020), pp. 197-205.

* cited by examiner

BODY-CONDITION-DEPENDENT STIMULATION WITH REAL-TIME COMMUNICATION BETWEEN AN ACTION MODULE AND A CAPTURE MODULE

The invention relates to a system for body-condition-dependent stimulation with real-time communication between an action module and a capture module. In this system, biological tissue is stimulated while at the same time signals of biological origin are captured. The use of this method and the assembly relates predominantly, but not exclusively, to all areas of medicine where bio signals are used for body-condition-dependent stimulation.

PRIOR ART

There are medical treatment methods, as described in WO 2017099603 (A1), using a focal neuromodulation technique for which the correct position on the cortex of the brain needs to be determined, which is appropriate for better treating psychological or neurological problems. This treatment can be implemented by transcranial magnetic stimulation (TMS) while measuring the heartbeat at the same time. When a systematic change in the form of a heart rate reduction (change in heart rate variability) is recognizable, the position is deemed to be found. The heart rate is displayed in immediate response to repeated pulse sequences of repetitive TMS.

For detecting this stimulus-response pattern, immediate measuring is required to correctly correlate the response to the stimulation and thus be able to draw the right conclusion regarding the medically suitable positions for the location of the stimulation.

However, the specification does not disclose how to technically implement the immediate response and/or the quick feedback.

Typically, the modules for action (stimulation by TMS) and capture (measuring of ECG) are connected to one another by means of a commercially available bus system. However, this does not make it possible to ensure immediate communication and, moreover, communication in real time.

In a different context, there are Ethernet transmitters as described in the journal "Elektronikpraxis" no. 8 from 16/04/2019 on p. 19, forming a protective device, for example by means of galvanic isolation.

Based on known systems for body-condition-dependent stimulation, it is the object of the invention to provide a system that allows performing body-condition-dependent stimulation in comparably reliable and safe manner.

This object of the invention is achieved by a system according to claim 1. Preferred embodiments are explained in the dependent claims.

Bio data is data generated by measuring biological parameters. Biological signals are bio data as well, in particular a data stream of various continuous-time or discrete-time measurements providing valuable information on the condition of tissue or an organ. In this context, such data or signals provide information on the functions of organs within an organism (e.g. ECG, EEG, EMG, EOG, ERG, PPT, respiration, MCG, MEG, BP, SpO2) which supports measuring an effect of a previous (or quasi-simultaneous) stimulation on the body. Apart from adequate signal processing, feature extraction and targeted impact on the human body, prerequisites for the quality of body-condition-dependent stimulation (following the measurement) include artifact-free and interference-free stimulation, which is guaranteed by the system according to the invention due to the real-time requirement (immediacy) for communication between the capture modules and the action modules of the system.

Depending on a therapeutic requirement, bio signals are derived from locations on the body. This may be done, for example, on the head (EEG) as well as on the body (e.g, EMG, ECG, BP, SpO2).

During a typical treatment, the bio signals are recorded continually before, during and/or after a medical intervention by sensors of the same type but also of different types. The time gaps here may range from immediately, that is, within microseconds to milliseconds, to minutes or hours.

By amplifying signals and preparing them for digital signal processing, for example, artifact-free signals and information relevant for a therapeutic intervention may be obtained. Parameters here include, for example, changes in the current band performance, amplitude, frequency and/or phase in the electroencephalogram (EEG), the individual alpha frequency in the EEG, the systolic interval of the continuous blood pressure (abbreviated by BP), the effective value of the EMG, the pattern of the photoplethysmographic signal, the oxygen saturation in the blood (SpO2) and further parameters, which may be combinations thereof.

Sensors for capturing/measuring the bio data, bio signals or signals of biological origin are preferably located within the capture module, also referred to as the capture unit. In advantageous designs of the invention, such a module, also referred to as a function module herein, may be designed having an interface for connection to a real-time bus, in particular an EtherCAT bus. For this, the function module has an interface portion, which includes the interface to an externally connectible device or to a device integrated within the function module or to a downstream piece of equipment. Furthermore, such a function module has a connection and control portion. Preferably, this connection and control portion has a micro controller as a control unit for the function module and a contact portion designed for connecting to the real-time bus of the device.

The signal processing or evaluation of the bio data or bio signals may either take place already within the capture module or only in the action module or in a separate evaluation module, also referred to as a signal processing module or master module, which communicates with the action module and the capture module via the communication link.

The action module comprises, for example, actuators which can exert an effect on the tissue and/or the organs and/or the body in general. The action module may also provide only the interface to such actuators, wherein the actual actuators, in turn, are then connectible to the master module as external components.

Basically, the biological organ or tissue may be influenced by electric, magnetic, electromagnetic, mechanical, pneumatic and/or hydraulic actuators, for example. Electric currents are introduced and/or applied into or onto the locations on the body by electrodes, magnetic fields by coils, mechanical forces by actuators, gases and/or liquids by hoses and/or lines.

For stimulation depending on the body condition, a feedback is required, for example, that allows the bio data or bio signals to influence the way in which the actuators are controlled. A suitable controller or control loop (closed loop, if required) is recommended for this purpose.

The following aspects may be taken into consideration here:

preferably, the actuators are able to quickly respond to information regarding the body condition (the bio data or bio signals) for a body-condition-dependent stimulation;

preferably, the actuators output only those signals that are relevant and/or desired for influencing the human body/ the organs;

preferably, the signal levels of the stimulation are present as time-discrete and/or value-discrete digital signals, which are output to the actuator in the form of mechanical and/or electromagnetic energy after being converted and amplified (adapted);

after being converted, the signal levels for capture are present in the range of nanovolts to millivolts within a frequency band of zero to several kilohertz, for example;

in the frequency band used (for example used for feature extraction from the EEG), heavy interference signals may be caused by stimulation and the environment; according to the invention, these interference signals may be taken into account and may be filtered out as required;

the signal sources to be examined, for example of electrophysiological origin, are preferably of high resistance;

the physical properties of, for example, the stimulation and capture electrodes change over time (e.g. by changing electrode transition impedances, electrode voltage, offset potentials, contact pressure conditions or by motion artifacts).

There are known stimulation and signal capturing systems that partially overcome these problems by carefully selecting the methodology for derivation and the respective technology for amplifiers, evaluation and stimulation. However, high-quality commercial stimulation and polygraphy systems for body-condition-dependent stimulation and simultaneous recording and evaluation of bio signals of different physiological origins are highly cost-intensive and only intended for stationary use in most cases.

Hereinafter, as an example of body-condition-dependent stimulation based on the capture of signals of biological origin, the current approach using actuators and sensors will be discussed.

Nowadays, electrical stimulators for cranial electrotherapy are implemented as constant current sources controlled by microcontrollers. This allows electrical stimulation using any desired form of current. To generate the analog electrical signal, the forms of current are provided digitally by the microcontroller program. If there is insufficient scanning and the dynamic range is too small, the required digital-to-analog conversion may lead to systematic errors in the analog electrical signal for the stimulation and cause undesired frequency lines in the EEG spectrum.

Measuring the EEG during electrical stimulation also makes high demands to the EEG's derivation technology and the derivation of the EEG. Demands to EEG measurements include, for example:

avoiding saturation of the amplifier by sufficient amplitude resolution;

avoiding mains interferences by using battery-powered capture units;

avoiding the interfering capacitive impact of the outer dermal layer on the signal by careful preparation of the skin.

In other applications, for example in ECG measurements, the same demands or part of these demands may apply as well.

In general, present assemblies have at least one of the following drawbacks:

slow processing since there is no real-time system for body-condition-dependent stimulation that can perform artifact correction and feature extraction at the same time;

instability with smaller, in particular non-consistent delays for a feedback-controlled/regulation-coupled application;

complexity in case of considerable testing or adaptations being required after changes made to the set-up or the operating system.

In one embodiment, the invention provides a system for body-condition-dependent stimulation having two function modules, for example an action module for stimulating tissue and a capture module for deriving/measuring bio data or bio signals, in which the two modules communicate via a communication link that meets hard or at least firm real-time requirements.

The action module and the capture module may have, for example, processor means for data processing such as a central processing unit (CPU). In addition, they may be equipped with electronic data memories for data storage such as a flash memory or a solid-state disk (SSD).

Both modules may be combined in a single housing and may form components of a single device. However, it may also be intended for the action module and the capture module to be formed separately and/or portable, for example, in order to facilitate connection to a patient.

The bio data or bio signals captured by the capture module may be analyzed more in-depth by means of an evaluation assembly. This evaluation assembly may be set up locally at the capture module, for example as a component in a device, or remotely, for example at a computer desk. A communication link between the capture module and the evaluation assembly may be wired by means of fiber optic cables, copper wires or direct by printed circuitry in a suitably integrated device; however, it may also be established by radio, for example via one of the standards GPRS, 3G, 4G (LTE), 5G, 6G, as long as the necessary requirements regarding time, in particular real-time requirements, can be met.

Analysis and output of the data, for example on an integrated display device, may be less up-to-date than the communication between the master module and the function modules, in particular if only a measurement and no stimulation-dependent feedback modulation is required, so that, for example, in one design of the invention, data transmission without real-time capability and with latency periods of over 100 ms is sufficient as well.

Suitable protocols for data transmission to external evaluation units may be TCP/IP, for example, in order to use the Internet or Ethernet. When using the Internet for data transmission, patient-related data will preferably be encrypted for transmission.

In terms of a telemedicine application, a remote evaluation assembly makes it possible that, for example, an expert for the evaluation of bio data or bio signals does not have to be present on-site during data capture from a patient, but may rather assess real-time measurements in a remote location, that is, away from the patient. In this way, the invention may be used even more universally.

The evaluation assembly may be set up, for example, as a server having a CPU and a data memory. Analysis of measured data, which is transmitted by the capture module, can be done via software. However, the evaluation tool may also be present as a software-only component in a cloud. A cloud is a computer network including many data processor and data memory resources which are controlled from a central location and scalable, i.e. they can be made available to an application as required. This embodiment has the advantage that many different data sets of different patients (made anonymous, if required) may be collected and compared.

The evaluation assembly may include software for machine learning, i.e. for example for a neural network and "deep learning", in order to identify a pattern from the captured data of a patient or of many patients (in particular with a cloud-based solution). For example, such patterns may relate to characteristic waveforms in the EEG as a result of stimulation by the action module when an electroencephalogram (EEG) is captured, i.e. electric currents to be derived by electrodes on the scalp of a patient.

In other words, the system according to the invention guarantees that the real-time requirement (immediacy) for the communication between the modules of the system will be met. Due to the simultaneous capture of bio data and body-condition-dependent stimulation according to the invention, stimulation of the human body may be performed more often or more target-oriented. Moreover, it is possible to allow releasing a trigger pulse according to predetermined parameters, for example by means of a control module.

The capture module must be able to free the EEG signal from the artifacts quickly and in real-time during electrical stimulation.

For this, the technology for capturing signals with high dynamic ranges (1 pV to 250 mV) is just as important as expertise about the creation and interpretation of the artifacts by electrical stimulation and how to avoid and/or eliminate them. In addition, information on the behavior of the action module must be available as well, as it may behave as predicted or there may be (indirect) communication from the action module to the capture unit. Such a flow of information between the modules would again be established via the real-time bus, so that a piece of information from the action module would be uploaded into a data packet of the master module, which would then be made available for download from the next data packet to the capture module in a follow-up packet, usually one millisecond afterwards with the preferred clocking according to the invention of the integrated stimulation and measuring system (MIS).

In particularly preferred designs of the invention, data processing, removal of artifacts and the like are performed within the master module. In this context, the function modules are used, for example, to capture data and send them to the master module, to control actuators according to the commands from the master module or to release trigger signals for controlling external devices. In this way, a real-time execution of the commands from the master module can be improved, for example, as there is no need for the function modules to perform complex calculation steps.

Furthermore, filter algorithms may be required or advantageous for the combined measuring of the EEG during stimulation (e.g. by tES), which need to be used in the real time provided by the system according to the invention and allow hardly any delay between the occurrence of the event and the extracted feature. These algorithms must meet the requirements in terms of both speed (target: short delay) and interference suppression (target: good signal reconstruction). Dynamic regression models are not used here since they require a template and may thus be subject to a delay of several seconds. Such a template is a pattern describing the artifacts in general and which is formed by measurements. Since the bio signal can never be predicted, the impact of the artifact on the bio signal needs to be estimated.

Here, the removal of artifacts from the measuring signals, which are mainly caused by external impacts from the environment but also by the stimulation trigger(s), is dependent on the modalities of the neuromodulation, among other factors, for example whether TMS or tES measuring methods are used. Depending on the application case, these methods may be, for example, recursive methods for filtering, FIR filtering and the like, when the measurement is to be performed during neuromodulation.

In a preferred embodiment of the system according to the invention, the capture module includes a filter device. The filter device may be designed, for example, as a band-pass filter filtering interference signals out of the captured bio data or bio signals. Interference signals may have frequencies that are out of range of a predefined frequency interval, for example. A frequency interval has an upper and a lower threshold for the amplitude.

Furthermore, interference signals may have amplitudes that are outside of a predefined amplitude interval, for example. An amplitude interval has an upper and a lower threshold for the amplitude. The filtered-out interference signals are then disregarded in further analyses, thus improving the quality of downstream analyses.

Artifacts in stimulation by the action module may also be detectable as interference signals and filtered out. Since the temporal development of the artifacts is basically known based on the known stimuli delivered by the action module, they may be filtered out in real time in an refinement of the invention. For example, in a transcranial stimulation using electromagnetic pulses, the radiation pulse sequence could be filtered out or calculated out of the captured bio signals or bio data. The effect on derivation electrodes on the head of a patient caused by using transcranial stimulation, for example, may be determined by direct induction when in this case the action module and the capture module are disposed close to one another at the head of a patient.

Other types of artifacts that may be identified and filtered out comprise, for example, interferences due to the electrical activity of the heart. When an electrocardiogram (ECG) is recorded at the same time as the EEG, these artifacts may be calculated out as well.

In advantageous refinements of the invention, the real-time capability might by optimized such that, for example with a data packet rate of 1000 Hz, that is, one date packet per millisecond, no prediction of the effect of measurements or stimulation is required since the high temporal resolution and the exact time of the measurement and/or stimulation allow an immediate consideration of the artifacts.

Stimulation techniques include TMS (transcranial magnetic stimulation), which is a non-invasive neuromodulation technique that has a direct influence on the function of the brain. Short magnetic pulses are directed to the head of a patient in order to induce electric currents in the underlying neurons.

Likewise, other electrical stimulation techniques such as nTMS (navigated transcranial magnetic stimulation), tDCS (transcranial direct current stimulation), tACS (transcranial alternating current stimulation), tRNS (transcranial random noise stimulation), DBS (deep brain stimulation), FES (functional electrical stimulation), ultrasound may be used on the head but also in peripheral regions (arm, leg, chest, neck) etc.

Examples of future uses of individual, patient-specific adaptations of brain stimulation/neurostimulation by means of electric currents (tES) to the brain activity patterns (EEG) may include the preferred embodiments of the invention discussed below.

In a preferred embodiment of the system according to the invention, the capture module is designed for deriving and/or measuring an EEG. This is an advantage, as an EEG makes it possible to determine the brain activity, and based on this, neural stimulation may be performed, for example. This is commonly referred to as neurofeedback.

Measuring the EEG may be performed by means of an electrode assembly for capturing brain waves. For this, the electrode assembly may include a plurality of electrodes, preferably more than 10, which are connected to an analog-to-digital converter in like manner. For example, the electrodes may be attached to a hood such that a vast number of different regions of the brain may be monitored for electrical activity. The electrodes may each have an actuator to press them onto the head of a patient. The actuator may be controlled electromechanically. Preferably, each actuator is connected to a compressor by a fluid-tight hose. The compressor may generate overpressure within a fluid, for example a gas such as air, so the actuator expands and presses the electrode onto the head. For this, each actuator may have a pneumatic cylinder or a plastic cushion that can be filled with air.

The advantage of performing the pressing in pneumatic fashion using pressurized air is that a particularly uniform pressing is achieved for each individual electrode of the hood.

In a preferred embodiment of the system according to the invention, the action module is designed for transcranial stimulation of tissue. In this context, the term "transcranial" refers to acting on tissue through the cranial bone. The affected tissue may be the brain of a patient, for example.

In a preferred refinement of the aforementioned embodiment, the action module is designed to imprint a brain rhythm from outside by means of transcranial alternating current stimulation (tACS).

In another preferred refinement of the aforementioned embodiment, the action module is designed to trigger phase-related transcranial magnetic stimulation for targeted inhibition or excitation of corticospinal tracks.

In another preferred embodiment of the system according to the invention, the capture module is designed to perform a measurement of the individual EEG alpha peak frequency (iAPF). The measured iAPF allows, for example, repetitive control of the action module for scientific studies on the treatment of persons suffering from depression. In this context, the action module may perform stimulation by means of transcranial magnetic stimulation.

Furthermore, other applications can be used:

capture of EEG and phase-related TMS for scientific studies on the treatment of persons suffering from depression;

development, implementation and evaluation of exact and/or fast techniques for correcting artifacts (tES) in the derived bio signal (EEG);

development and implementation of self-calibrating, low-noise and real-time-controllable power sources for tES;

implementation and evaluation of techniques for phase-exact detection of events in the EEG;

development and implementation of a generic platform for an integrated stimulation and measuring system (MIS) for combined EEG measurement and multi-channel alternating current stimulation.

The central aspect of the invention relates to communication between the capture modules and the action modules via a communication link (wired or wireless) that meets hard or at least firm real-time requirements. Since biological procedures include a temporal component as well, stimulation can only be performed usefully in an adaptive way when the data on which the adaption is based is provided in due time (firm real-time requirement). For this, the measurement needs to be performed within certain time limits after stimulation, and furthermore the measuring results need to be evaluated and supplied to the action module for follow-up stimulation within another time limit.

A hard real-time requirement is defined as follows. Exceeding the response time is considered a failure. After an exact determination of the time for the application to be provided, calculations according to the theory of the real-time systems will be required. Real-time systems always give the correct result within the given time limits. Users can rely on this quality when using a hard real-time system. A firm real-time requirement, on the other hand, is defined as follows. With firm real-time requirements no immediate damage is to be expected. Once the time requirements elapse, however, the result of the calculation is useless and may be discarded.

It is possible to use a firm real-time requirement for the entirety of measurements, where individual measurements that do not meet the hard real-time requirement are discarded and/or not taken into account for the analysis to be output.

In this case, discarding measurements is relevant only for data evaluation. The samples as such are kept and the closed-loop method is not interrupted.

A real-time measurement is intended to allow the possibility of an immediate evaluation and/or observation of the signals. In one embodiment for measuring an EEG, the components are designed for frequencies up to 600 Hz. In order to be able to detect such frequencies, the requirements for scanning according to Shannon must be guaranteed.

In particular with bus links, i.e. with more than 2 participants, meeting hard real-time conditions in communication links may be challenging, for example because there might be collisions during sending by participants. Time slicing methods or polling are typically recommended methods here.

A widespread and thus proven and low-cost bus system is Ethernet, which expects collisions and time delays due to its CSMA/CD and is not real-time-capable per se.

There are extensions of Ethernet standard such as standards from the field of Timesensitive Networking (TSN), providing real-time capability. Widespread standard hardware can be used here since the TSN part operates on a higher layer of the protocol (ISO/OSI model).

Alternatively, specialized systems are available on the market, which are optimized for higher speeds and real time, such as Infiniband, which is used with supercomputers and allows a very low latency better than TSN.

According to the invention, the use of an EtherCAT bus system as the communication link for the capture modules and the action modules is proposed.

The bus system EtherCAT, which is an international IEC standard, is regarded as the "Ethernet field bus" as it combines the advantages of Ethernet with the simplicity of the classic field bus systems, avoiding the complexity of IT technologies.

EtherCAT circumvents the drawbacks of Ethernet by the particularly high-performance operational principle: in general, one frame is sufficient to update the output information in all participants and read the input information for the control within the same frame. The telegram sent by the EtherCAT master passes through all participants. Each EtherCAT slave reads the output data sent to it and puts its input data into the forwarded frame on the fly. The telegram is delayed only by hardware processing times. The final participant of a segment (or branch) identifies an open port and returns the telegram to the master-here, the full-duplex property of the Ethernet architecture is exploited. Advantageously, all connected modules (slaves) are physically connected directly to the master via the real-time bus (MAC-to-MAC communication). This allows direct communication between the function modules and the master without looking for ports or other delays caused by communication protocols.

As a result, the maximum payload rate of a telegram is higher than 90%, and the theoretical effective data rate by exploiting the full-duplex property even exceeds 100 Mbit/s (>90% of two times 100 Mbit/s). The EtherCAT master is the only participant in the segment allowed to actively send an EtherCAT frame; all the other participants are just forwarding the frames. This prevents unpredictable delays and guarantees real-time capability. Note that this does not mean "forwarding" in the usual sense though. According to the invention, there is no stopping of the signal in any of the function modules. Instead, the set-up makes it possible for the data packets to simply pass through the individual modules, as mentioned above, and for the modules to download data from the frame and upload data to the frame at this time.

The master uses a standard Ethernet Medium Access Controller (MAC) without an additional communication processor. In this way, a master can be installed on any hardware platform providing an Ethernet port. In this case, the real-time operating system used or the application software are not relevant. The EtherCAT slaves use an EtherCAT Slave Controller (ESC) for the on-the-fly processing. This means that the processing is entirely done in hardware, making the performance of the network predictable and independent from the implementation of the individual slaves.

The master generates the data packets here according to the network architecture. In this way, the configuration of the modules may be specified once-only in the bus and stored in the master, at least in one preferred embodiment of the invention. After this installation, the data packets may be generated and suitably processed according to the actual physical arrangement in the bus system. This means that the modules can download and process the commands specifically directed to the respective module and upload data accordingly into the passing data packets.

This makes it possible for the generated frame to reach all modules at virtually the same time, constrained only by the physical passing time of the data packets through the lines. A frame, that is, such a data packet, may reach all function modules within the real-time bus in less than 100 ns, preferably less than 50 ns, in particular less than 20 ns, for example within 15 ns.

The EtherCAT bus system may thus have the required capabilities for the applications mentioned and in particular for applications of the system according to the invention:
the update time for the data of 1,000 distributed inputs/outputs is only 30 µs-including terminal passing time;
a single Ethernet frame allows the exchange of 1, 486 bytes of process data-equaling almost 12,000 digital inputs and outputs. Transmitting this amount of data consumes only 300 µs;

performance 256 digital I/Os in 12 µs, 1,000 digital I/Os in 30 µs, 200 analog I/Os (16 bits) in 50 µs, equaling 20 kHz sampling rate, 100 servo axes every 100 µs, 12,000 digital I/Os in 350 µs.

In a preferred embodiment of the system according to the invention, a wired data communication via fiber optic cables or copper wires is used for the communication link between the action module and the capture module. This has the advantage of a comparably reliable, safe and fast data transmission.

In an advantageous refinement of the system according to the invention, a radio-supported data communication according to the 5G standard or the 6G standard is used for the communication link between the action module and the capture module and/or the master module. This has the advantage that data transmission can be performed in real time despite using a radio connection.

According to an advantageous refinement of the invention, it is provided that, in addition to the action module for actuating actuators for stimulating tissue and the capture module for deriving/measuring bio data or bio signals, a control module for digital input/output control (DIO) of actuators of external devices, wherein the actuators are designed for stimulating tissue, and a master module for processing the module signals/data are also connected to the real-time-capable bus, in particular an EtherCAT bus, also referred to as ECAT. Furthermore, the modules are designed such that they exchange information with one another on the real-time-capable bus during the same calculation step at a clock pulse provided by the master module depending on the data processing of the same, and that the data/signals measured by the capture module, preferably an A/D converter, are sent to the master module and processed there, and that the master module sends data/commands to the action module in order to activate the stimulation of tissue via the actuators.

According to the invention, at least one function module is designed accordingly with an EtherCAT interface. In this way, the real-time conditions of the system, in particular the hard or firm real-time requirements for the device, can be met in an improved manner. Advantageously, a plurality of function modules, in particular all of them, involved in stimulation, measuring and/or evaluation include such a real-time-capable EtherCAT interface. Here, the function modules are connected to the master bus, in this case the EtherCAT bus, as "slaves" in a "master/slave configuration".

Within a while loop based on the EtherCAT bus, this system allows adapting the modules for signal measurement/capture, including capture of bio signals such as EEG, ECG, EXG etc., for digital input/output control of peripheral external devices and for the generation of analog signals for the actuators controlled by the action module such that they provide information for one another on the bus at the same time and/or during a single calculation step. Typically, this is repeated every 1 ms, based on the clock pulse of the bus and on the content of the data processing by the master module.

Advantageous embodiments of the modules of the system according to the invention provide
that the capture module (3, A/D module) comprises an A/D converter for converting analog bio data/bio signals captured by this module to digital signals to be processed in the master module; and/or
that the action module comprises a D/A converter for converting digital control signals provided by the master module to analog signals to be supplied to the actuators for stimulating tissue, and/or that, for digital input/output control, the control module controls the signal flow of digital control signals provided by the D/A converter of the action module and the master module by means of trigger signals generated by the master module and generated by the control module.

Based on known methods for body-condition-dependent stimulation, a further object of the invention can be to provide a method that allows performing body-condition-dependent stimulation in a comparably reliable and safe manner.

This object of the invention is achieved by a method according to claim 11. Preferred embodiments are explained in the dependent claims. The same advantages as explained in the introduction for the method according to the invention and the system according to the invention apply analogously here as well.

An advantageous method for body-condition-dependent stimulation based on the system according to any one of the system claims provides that the modules communicate with one another in a closed loop and the data of the action module have effects on the behavior/function of the capture module and vice versa, that the stimulation is composed of neuromodulation excitation/inhibition, that the action module controls magnetic, electromagnetic, mechanical, pneumatic and/or hydraulic actuators for directly influencing biological tissue or organs, that the action module performs multi-channel stimulation of biological tissue based on features from the bio data capture of bio signals of different origins by the capture module in a frequency range of 0 to some kilohertz, in particular up to 100, 200 or 300 kHz, and that the capture module is designed to capture EEG, ECG, EXG, EMG, EOG, ERG, PPT, respiratory, MCG, MEG, BP, SpO2 signals.

The invention further relates to a device including a control module and/or master module, a real-time master bus, a plurality of module slots, preferably at least two, but at least one module slot, as well as at least one function module, wherein the at least one module slot is connected to the master module 4 via a real-time-capable data connection and the at least one function module is designed with a real-time-capable interface and connected to the real-time-capable master bus. Here, the real-time-capability can be provided such that hard or firm real-time conditions are met. Furthermore, the at least function module is designed to send the data to be processed to downstream internal and/or external components such as data capture devices, measuring units, output devices etc. by means of hardware or software, preferably under the same real-time conditions.

According to the invention, a system for body-condition-dependent stimulation having a feedback loop for time-exact stimulation of biological tissue and/or for reading bio signals or bio data in a feedback-modulated signal capture, for example an EEG measurement, includes at least the master module connected to an AD module and a DA module.

If only a trigger were to be released at a predetermined time without additional stimulation, at least the master module connected to an AD module (capture module) and a DIO module (control module) would be required.

For more advanced applications such as real-time measuring of bio data intended to release a stimulation-dependent trigger, further modules may be provided one by one according to the invention.

Feedback and evaluation of certain features from bio signals allow signal- or status-depending changes in modulations. The specific parameters are dependent on the actual application case. Examples of this include: analysis of the individual alpha frequency in the EEG and release of a trigger signal for a TMS device at a phase of 90° in the EEG; or analysis of a heartbeat in the ECG and release of a current pulse in the systolic interval. In doing so, the amplitude, the frequency and the phase can be analyzed in the EEG, for example.

In the ECG, the amplitude, the time of the R wave and the time gaps between R waves can be analyzed.

Advantageous developments and further exemplary embodiments will be described and explained in more detail with reference to the attached figures below.

IN THE FIGURES

Figure 1:
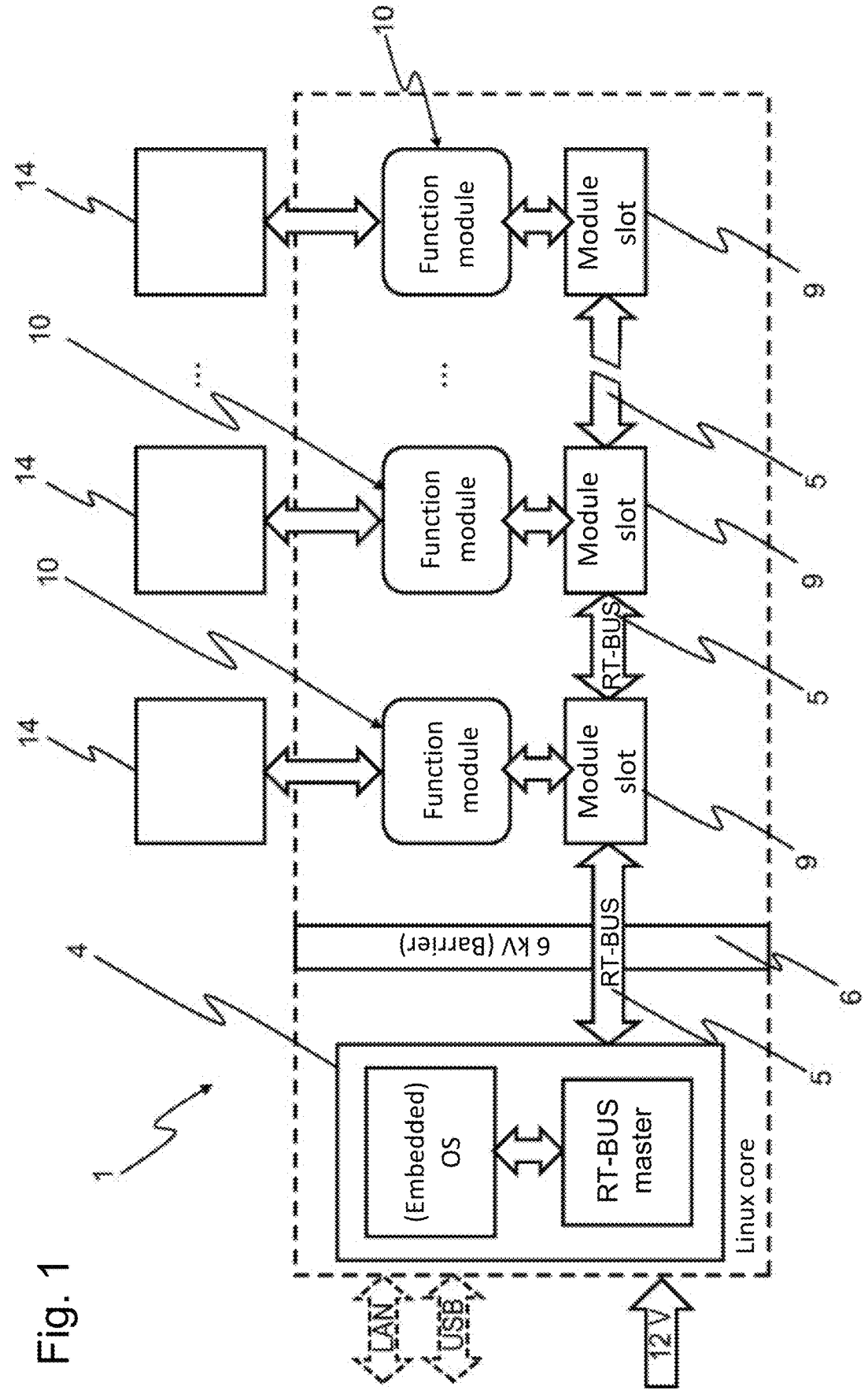
FIG. 1 shows an integrated stimulation and measuring system (MIS)

FIG. 1 shows a schematic representation of an integrated stimulation and measuring system (MIS) 1 according to the invention. The MIS 1 may be designed as a device having a housing, indicated by the dashed framed outline in FIG. 1. The MIS 1 includes a signal processing module 4. The signal processing module 4 has a real-time bus master and a calculation unit. The calculation unit may be a computer chip having an operating system installed thereon. Advantageously, the signal processing module 4 has a Linux core with an embedded operating system (Embedded OS). The signal processing module 4, also referred to as master module, may include an embedded board, for example, having a clocking of 800 MHZ-1 GHz. It is understood that other clockings are conceivable as well as long as they meet hard or firm real-time requirements applying for the relevant intended demands.

The real-time bus master, also referred to as RT-BUS master in FIG. 1, is connected to a plurality of module slots 9 via a real-time bus 5. Each module slot 9 is designed and provided to receive a function module 10. In this context, a function module 10 is any module designed to enable the function of the MIS or expand the functionality thereof.

FIG. 1 exemplifies three module slots, but there may also be more or less modules provided in the MIS. In this regard, at least two function modules 10 may be provided, for example, for use of the MIS according to the invention. The function modules 10, in turn, are connected to integrated or external components 14. These components 14 may include actuators, capture devices, display devices, electrodes, etc. For example, the components 14 might allow or implement the following functions: EEG measurements, setting of trigger signals and/or reading of trigger signals, power supply to the MIS and/or one or more of the components 14, data capture, data processing and/or data transfer, display of data, function menus or other information, maintenance and/or control functions for the MIS and/or one of the connected components 14 and/or control functionalities, in particular touch-sensitive control of an integrated display device.

The double-pointed arrows with solid lines shown in FIG. 1 represent communication links preferably meeting real-time conditions. Accordingly, the communication link between a module slot 9 and a function module 10 is forced to meet hard or firm real-time requirements in order to allow the real-time operation of the MIS according to the invention. The double-pointed arrows with dashed lines shown in FIG. 1 represent further data connection interfaces that usually do not meet real-time requirements, a USB interface and a LAN interface in the drawing. Moreover, a power source of 12 V is indicated in FIG. 1.

Figure 2:
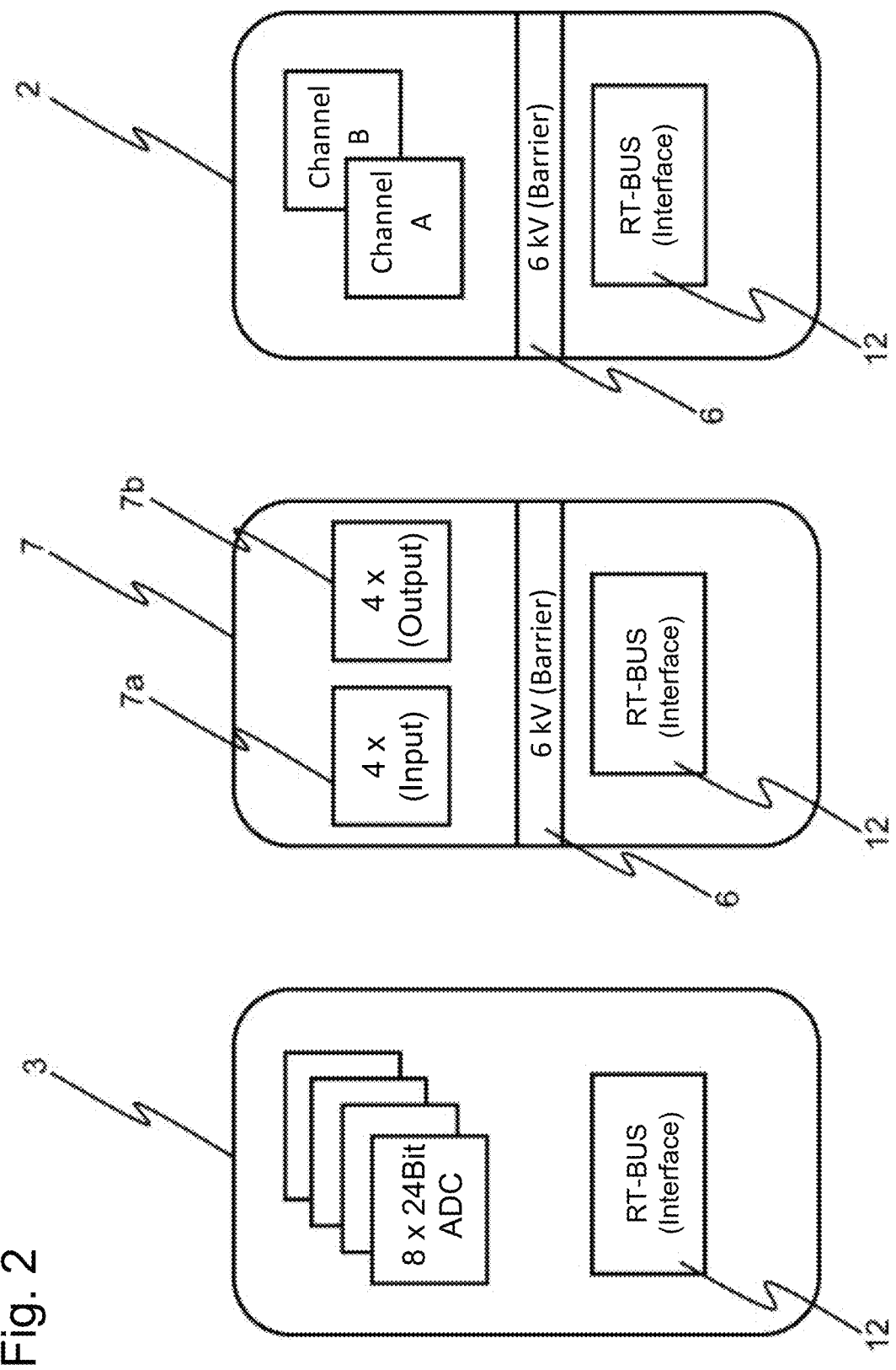
FIG. 2 shows a first module overview of different modules of the MIS.
Figure 3:
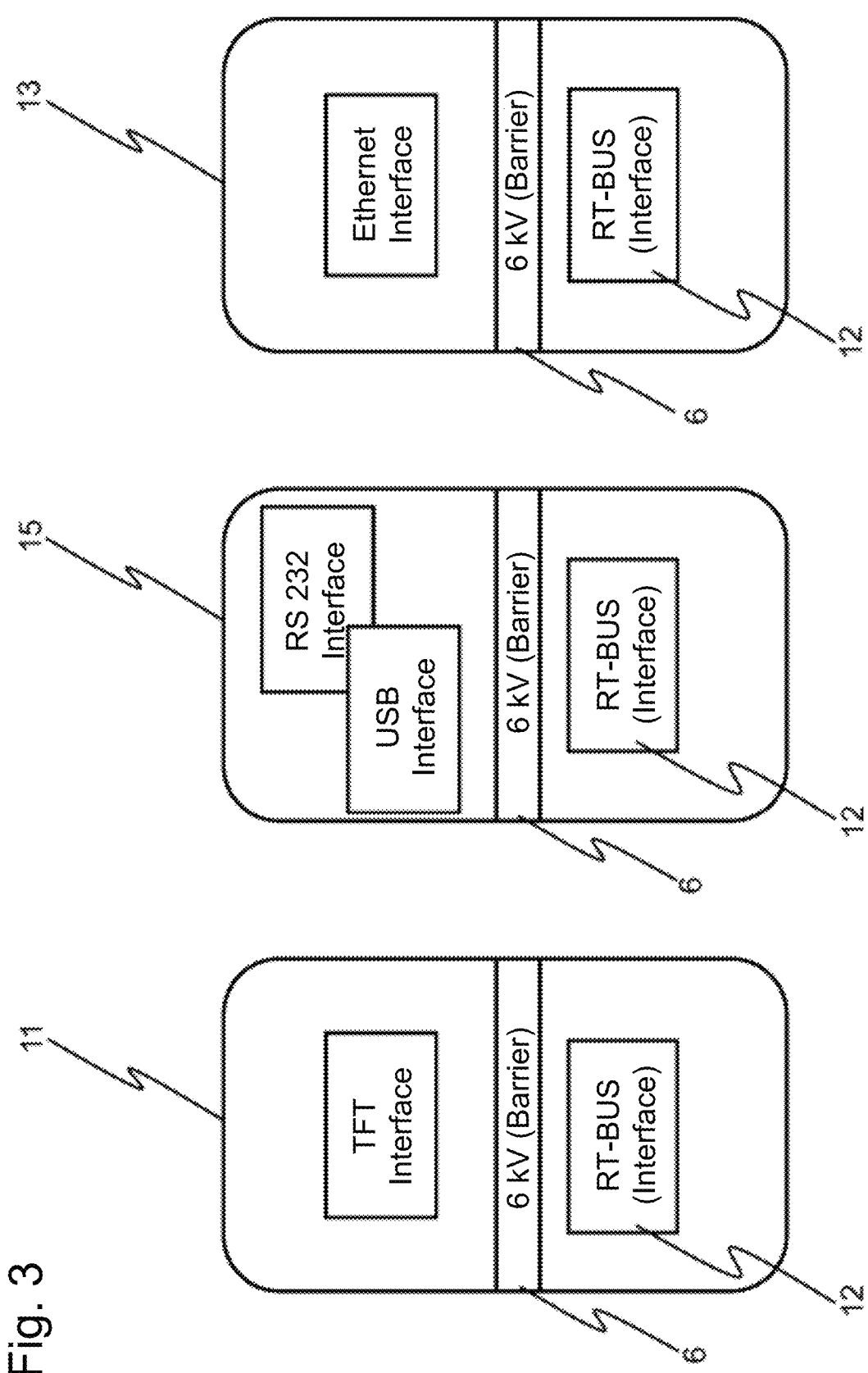
FIG. 3 shows a second module overview of different modules of the MIS.

As shown in the embodiment according to FIG. 1, the integrated stimulation and measuring system (MIS) 1 is implemented in the form of function modules 10, which may be enhanced as desired on both the capture side (capture module 3) and the output side (action module 2) without compromising the capacities for time-exact and accurate data processing between one another (cf. FIGS. 2 and 3). The modules communicate via the shared communication link 5, a real-time bus.

The function modules 10 may be used for electrical stimulation, control of electric, mechanical and/or pneumatic actuators, triggering of events, data capture, output and display of data and the like. A function module may also be designed for graphics processing, as a power source module or as a 3D acceleration module, for example.

Thus, the MIS 1 is a generic platform which may also allow examinations in other fields of medical technology by enhancing the parameter range for the capturing of bio signals and developing other forms of output. This can be accomplished by integrating further function modules designed for capturing predefined parameters, for example. Moreover, it is conceivable for the functional scope of present function modules to be changed or expanded by adaptation of their control and/or programming.

In advantageous refinements of the invention, the MIS 1 according to the invention may be designed for one or more of the following applications:

imprinting the brain rhythm from outside by means of transcranial alternating current stimulation (tACS) and triggering phase-related TMS for targeted inhibition or excitation of corticospinal tracks in real time;
    measuring the individual EEG alpha peak frequency (iAPF) and repetitive control of the TMS device with this frequency for scientific studies on the treatment of persons suffering from depression in real time;
    capturing of the EEG and triggering of a phase-related event, e. g. TMS pulse, for scientific studies on the treatment of persons suffering from depression in real time;
    capturing of the EEG and phase-related electrical peripheral stimulation (FES) for rehabilitation;
    capturing of the blood pressure (BP) and phase-related electrical peripheral stimulation for pain treatment;
    capturing of respiration or respiratory signals and corresponding stimulation of the midriff.

Based on the MIS, feedback-coupled modulation (stimulation) of the brain function can be accomplished on the basis of the individual physiology of the patient observed in real time. Investigations show that the implementation proposed herein does not only allow faster use, according to the invention in a closed-loop set-up, that is, a closed loop with rates of <1 to 3 ms for capture and processing of the EEG and triggering of an event. Higher time accuracy during capture and repeated stimulation is possible as well, without prediction for the future, as is common with current systems, being required. The deviation of the phases from the desired trigger times based on the captured measured data, which can be achieved with an MIS according to the invention, may be +/−5° at a frequency of 4 Hz, +/−12° at a frequency of 40 Hz, depending on the frequency in an EEG measurement. In an ECG detection of the systolic interval, a deviation may be +/−3 ms, for example.

Substantial advantages and advantageous refinements of this arrangement, in particular with respect to traditional solutions, may be as follows:

the entire signal processing chain (data capture-forwarding-processing-forwarding-action) is embedded within the real-time bus and can be synchronized by the same;
    due to the real-time bus, the four stages can be supplied with new data in all modules at the same time (delayed only by the signal transmit time on the bus); due to the packet interval (clock pulse of the bus), there is a maximum delay between data capture and action from a packet interval on the bus;
    the capturing (using a capture module 3) may be adaptable to all conceivable signals of biological origin as the interface to the bus may be the same for all modules;
    control of actuators for stimulating biological tissue (using an action module 2) does not require prediction as these may also be coupled to the bus via an interface;
    modular set-up and any desired combination of capture modules 3 and action modules 2. Only the processing software must be adapted to the respective task;
    processing of data and control of the real-time bus may be performed in an embedded Linux OS (for example Toradex-SOM) directly within the device.

FIGS. 2 and 3 show examples of (function) modules that can be connected to the real-time bus (RT-BUS).

As a first example of a function module 10, FIG. 2 shows a capture module 3, herein designed as an EEG module for data capture (for example ADS 1299) and connection to the bus. This capture module 3 as well as the remaining function modules 10 include(s) an interface portion or function portion having interfaces for external devices 14 as well as a connection and control portion (RT-BUS interface) 12. In at least one preferred embodiment, the connection and control portion 12 includes a microcontroller (μC) (for example Infineon XMC48 xx).

In the embodiment shown, the interface portion includes four interfaces, each having 8 channels, thus provides up to 32 channels, for example for an EEG measurement. Each channel operates at a resolution of 24 bits. In alternative embodiments, the channels may also operate or be operated at other resolutions. Here, the EEG module 3 is an analog-to-digital converter (ADC) and is also referred to as an A/D module hereinafter. The capture module 3 is intended for a sample rate of 1000 samples/see, so that a time of 1 ms is allowed for each sample or data packet. The interface of the function portion to an external component may be wired, but in an advantageous refinement it may also be wireless, based on a sufficiently fast communication standard such as 5G or 6G, or it may be optical. This also applies to the other function modules in like manner.

The RT-BUS interface is provided and designed to be incorporated within a module slot of the MIS. In this way, the connection to the real-time bus of the MIS is established and the function module is integrated into the MIS.

For this purpose, the RT-BUS interface 12 of the capture module 3 has a configuration specifically developed for the capture module 3. Here, the microcontroller is used to control the function module 10 and the data connection and data processing for the real-time operation.

The remaining (function) modules integrated into the MIS have an analog set-up, that is, a function portion and a connection and control portion, as well.

As a further example of a function module 10, FIG. 2 shows a control module 7, also referred to as IO module or DIO module. The control module 7 is used to connect to the bus via a microcontroller (for example Infineon XMC48xx). The control module 7 shown here may in particular be designed for releasing or receiving one or more trigger signals and/or for setting a respective level for the trigger signal. In the design shown, the control module 7 includes 4 data inputs 7a and 4 data outputs 7b. Preferably, a transistor-transistor logic (TTL) may be provided here. The inputs and outputs 7a, 7b, in turn, are isolated from the bus by a galvanic isolation 6 using a digital isolator (e.g. ISOW78xx Infineon). Here as well as with the other modules and galvanic isolations, the galvanic isolation may be a 6 kV barrier, for example.

The galvanic isolations provided here and in the function modules in an advantageous manner allow the electrical insulation of a patient against the measuring device and/or the insulation of the individual components of the measuring device against one another. This can reduce interference signals and erroneous measurements.

FIG. 2 further shows an action module 2, referred to as electric module or current module herein. The current module is used as an actuator for stimulation by delivering currents. The current module here is illustrated with two channels (Channel A and Channel B). The proposed set-up uses power sources that are separated and thus have independent power supplies. In this manner, lower interference from the power sources can be achieved. These power sources may be self-calibrating, more low-noise and controllable in real time, for example within 1 ms with new parameters. Data buffering may thus be omitted. Again, the RT-BUS interface is galvanically isolated from the interface portion. Depending on the specifically desired embodiment with regard to a predetermined application, a duration of more or less than 1 ms may also be selected as the real-time interval.

FIG. 3 shows a function module designed as a display device, in particular as a TFT module 11. The TFT module 11 is used for connecting a display device to the bus. As described above, the connection is made via a microcontroller (for example Infineon XMC48xx) with galvanic isolation of the display device by means of a digital isolator of the ADUM1xx series (Analog Devices). In the design shown, the TFT module 11 includes a control for a TFT screen via FT813. The resolution for the display device here is 800×400 pixels, and it has touch detection.

In at least one advanced development of the invention, the display device is firmly integrated into the MIS. It is understood that other display devices may be incorporated as well, integrated firmly or provided as external devices. These display devices may have different features, for example be designed with or without touch detection, have different resolutions, be monochrome or colored, etc. Moreover, a plurality of display devices may also be provided.

FIG. 3 further shows a function module designed as a COM module (communication module) 15. The COM module 15 is used to connect to other, even non-real-time-capable, interfaces such as one or more USB or RS232 interfaces. Further interfaces are conceivable as well, for example one or more CAN bus interfaces, and in particular wireless connection interfaces to connect to external devices as well.

A further example of a module to be connected to the MIS 1 is a LAN module (network module) 13, as shown in FIG. 3. The LAN module 13 is used to connect to a traditional local network (Ethernet). For this purpose, the LAN module 13 includes a respective LAN interface and a port for a data cable. The present interface is an interface for a 100 Mbit LAN. It is understood that the interface may also be designed for other transmission rates.

A further function module 10 may be a power module to connect the MIS to a power source, for example. It is also conceivable for one of the modules to be designed as a capture module having an interface to an acceleration sensor. An acceleration sensor may be used to capture one or more frequencies of a tremor, for example, which is common with Parkinson's disease. Further interfaces and function modules to be incorporated into a real-time environment, which is provided according to the invention, are conceivable as well.

Data processing within the MIS 1 is performed digitally in its entirety. Simultaneous body-condition-dependent stimulation and capture of bio signals of different origins is possible by using various amplification factors and scanning rates. The modular concept of the function modules by the shared digital interface via the real-time bus allows any desired cascadability.

Data is not captured—as it is done in conventional systems—by time-multiplex; instead they may be captured simultaneously, but can also be scanned completely independent from one another due to the modular structure. In this way, it may possible, according to the invention, to trigger a stimulation pulse within extremely tight tolerances at a predetermined phase of a measuring signal while the signal is being captured and a pain stimulus, for example, is triggered in a patient.

For performing a measurement with tissue stimulation under real-time conditions, for example, at least the master module 4 and two further function modules 10 are required, in particular the capture module 3 for capturing the measured values and the action module 3 for stimulating tissue.

For performing a measurement with trigger signal under real-time conditions, for example, at least the master module 4 and two further function modules 10 are required, in particular the capture module 3 for capturing the measured values and the control module 7 for releasing a trigger signal.

The digital interfaces between the function modules allow a highly efficient galvanic isolation 6 of the measuring assembly from the output and evaluation equipment so that elaborate analog isolation amplifiers for guaranteeing technical safety during medical use are not required, without compromising safety with respect to the measuring subject (patient). This ensures compliance with the standard EN 60601-1 on general requirements for basic safety and essential performance.

Compared to conventional technology, the proposed solution has the benefits of a small design size and low power consumption. A primary reason for this is the fact that just a single central calculation unit, namely the master module 4, is required instead of several separate computers connected to one another. According to the invention, all modules required for measuring and stimulation can be combined within a single device inside a housing not shown here.

Figure 4:
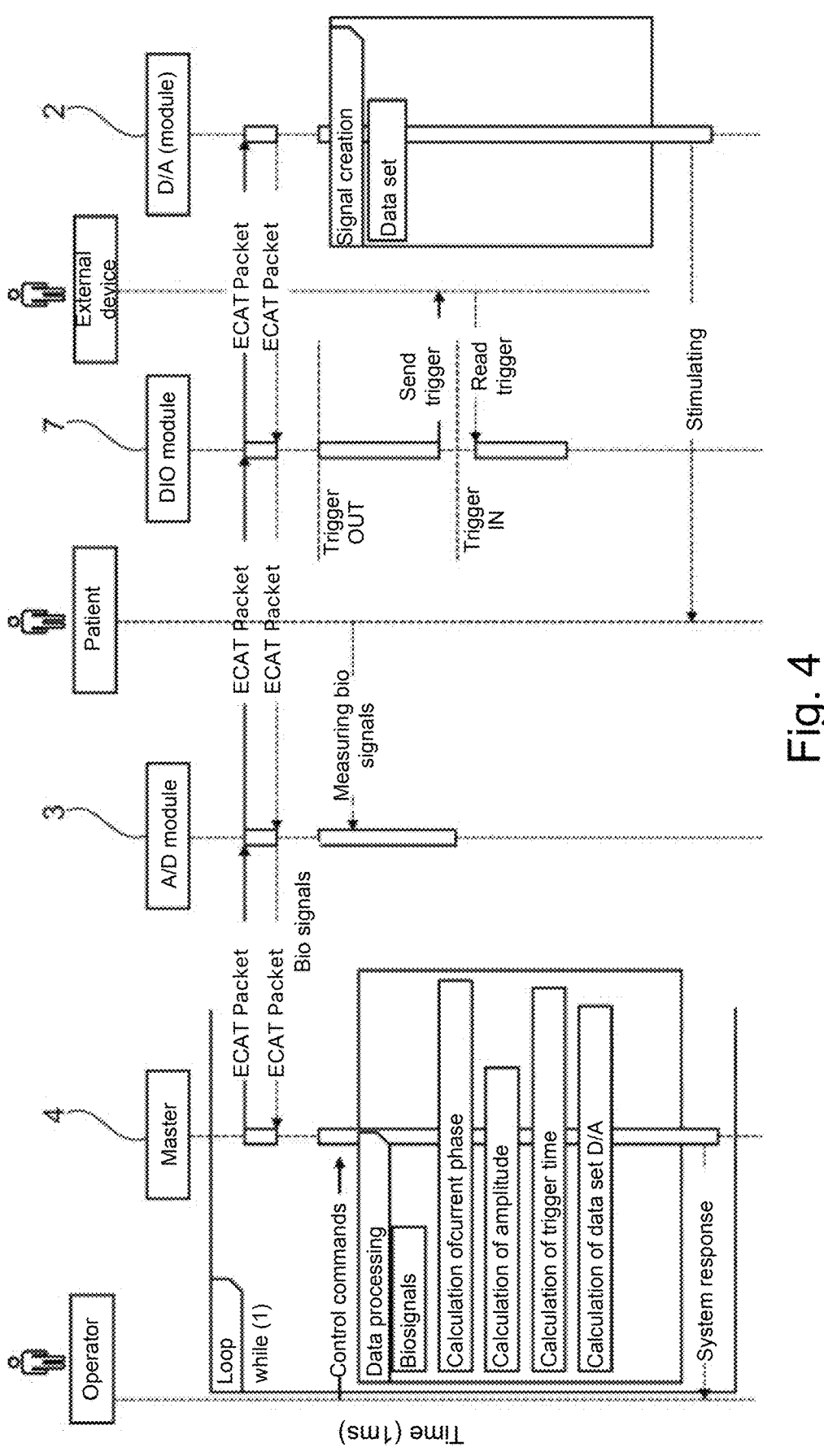
FIG. 4 shows an example of a closed-loop sequence for an embodiment of the integrated stimulation and measuring system.

FIG. 4 shows an example of a closed-loop sequence for an embodiment of the integrated stimulation and measuring system comprising a real-time bus. Preferably, the real-time bus is an EtherCAT bus, also referred to as ECAT in the figure.

In addition to the action module 2 of the real-time bus of FIG. 1 for controlling actuators for stimulating tissue, referred to as D/A module in FIG. 4, and the capture module 3 of the real-time bus of FIG. 1, referred to as A/D module for deriving/measuring bio data or bio signals in FIG. 4, a control module 7, referred to in FIG. 4 as DIO module for digital input/output control of actuators, for stimulating tissue, of external devices, and a master module 4, also referred to as Master in FIG. 4, are connected to the EtherCAT bus ECAT for processing the module signals/data.

The modules of the EthernetCAT bus ECAT are adapted to exchange information with one another on the real-time-capable bus (ECAT) during the same calculation step at a clock pulse provided by the master module 4 (Master) depending on the data processing of the same.

The data/signals measured by the capture module 3 (A/D module) are sent to and processed by the master module 4 (Master), and the master module 4 sends data/commands to the action module 2 (D/A module) in order to activate stimulation of tissue via the actuators connected thereto.

The capture module 3 (A/D module) comprises an A/D converter for converting analog bio data/bio signals captured by this module 3 to digital signals to be processed in the master module 4 (Master).

The action module D/A module comprises a D/A converter for converting digital control signals provided by the master module Master to analog signals to be supplied to the actuators for stimulating tissue.

The control module 7 (DIO module) performs digital input/output control of the signal flow of digital control signals provided by the D/A converter of the action module 2 (D/A module) and the master module 4 (Master) by means of trigger signals generated by the master module 4 (Master) and generated by the control module 7 (DIO module).

Within a while loop based on the EtherCAT bus, the system shown in FIG. 4 allows adapting the modules for signal measurement/capture, including capture of bio signals such as EEG, ECG, EXG etc., for digital input/output control of peripheral external devices and for the generation of analog signals for the actuators controlled by the action module such that they provide information between and/or for one another on the bus at the same time and/or during a single calculation step. Typically, this is repeated every 1 ms, based on the clock pulse of the bus and on the content of the data processing by the master module.

FIG. 4 shows an exemplary data loop of the measuring device in this context. Here, the time elapsed is illustrated in a vertical direction from top to bottom. The time illustrated here for such a data loop is 1 ms, equaling a frequency of 1000 Hz.

Of course, other frequencies are conceivable in other embodiments of the invention without departing from the idea according to the invention of meeting real-time conditions. Events arranged at the same height in a horizontal direction in FIG. 4 are taking place simultaneously or at least at approximately the same time.

As described above, the master module 4 generates a data packet that is sent to the function modules 10, here the capture module 3, the control module 7 and the action module 2, via the real-time-capable bus, in particular the EtherCAT bus. Here, the real-time bus is designed such that the data packets pass through the function modules, metaphorically speaking. During this passing, data is read from and written into the data packet by the function modules. This means that the function modules do not store the data packets temporarily and forward them afterwards. In this way, quasi-simultaneous receipt of the data packets may be achieved for all function modules.

Each of the modules is adapted to exchange information with one another on the real-time-capable bus (ECAT) during the same calculation step at a clock pulse provided by the master module 4 depending on the data processing of the same via a real-time-capable communication link 5. In this arrangement, the master module 4 is the only module allowed to generating a frame, that is, a data packet, while the function modules 10 downstream of the master module 4 can only read this frame and add data of their own.

Thus, in the closed-loop arrangement shown in FIG. 4, a data packet is generated by the master module and sent to the first function module, here the capture module 3. The data packet may contain a command for the capture module 3 to start capturing data, for example. The capture module will then start capturing data present in the form of bio signals of a patient.

In the course of this, the data frame already moves on from the capture module 3 to a subsequent function module 10, the control module 7 in FIG. 4, also referred to as DIO module. The control module 7 may control the digital input/output to actuators of the device, for example. In doing so, the control module 7 may generate a trigger, send it to an external device and/or read a trigger while the data packet has already moved on to the action module 2, which is shown downstream here.

The action module 2 receives the data packet, identifies the digital control commands of the master module 4 relevant for the action module 2 in the frame and converts them to an analog signal for actuators connected to the action module 2, generates a signal and starts stimulating a patient and/or sends a data set containing stimulation data to an external device, which may be connected to a patient for stimulation. Even before stimulation is performed, the data packet has returned to the master module 4, as can be seen in FIG. 4.

The master module 4 sends the frames or data packets at a given rate, for example one packet per ms, which are sent continuously in real time through the closed loop.

In this way, the data captured by the capture module 3 can be attached to a data packet and forwarded to the master module for processing so that the master module can output new control commands based on this data for the control module and the action module in one of the following frames, if required.

In the design shown, the capture module 3 includes an A/D converter for converting the captured analog data, here, the bio signals of a patient, to a digital signal for further processing.

Here, the data processing by the master module 4 may include a calculation of a current phase, an amplitude, a trigger time or a digital/analog data set. In this way, the master module 4 can define, change or adapt trigger times based on the received data. It is also conceivable to generate trigger cascades, for example, adapted to the bio data, in this manner. Moreover, the real-time system according to the invention and/or the device according to the invention allow(s) combining combinations of trigger signals, captured data and stimulation data on time scales not feasible before. This may allow an improved analysis of biological, biophysical and/or biochemical phenomena.

The master module 4 may be connected to an operator and receive control commands therefrom. The operator may be, for example, a person performing the measurement or a control device such as a digital one. Advantageously, this makes it possible to perform semi- or fully automated measurements. The master module 4 delivers a system response based on the data processing to the operator.

Figure 5:
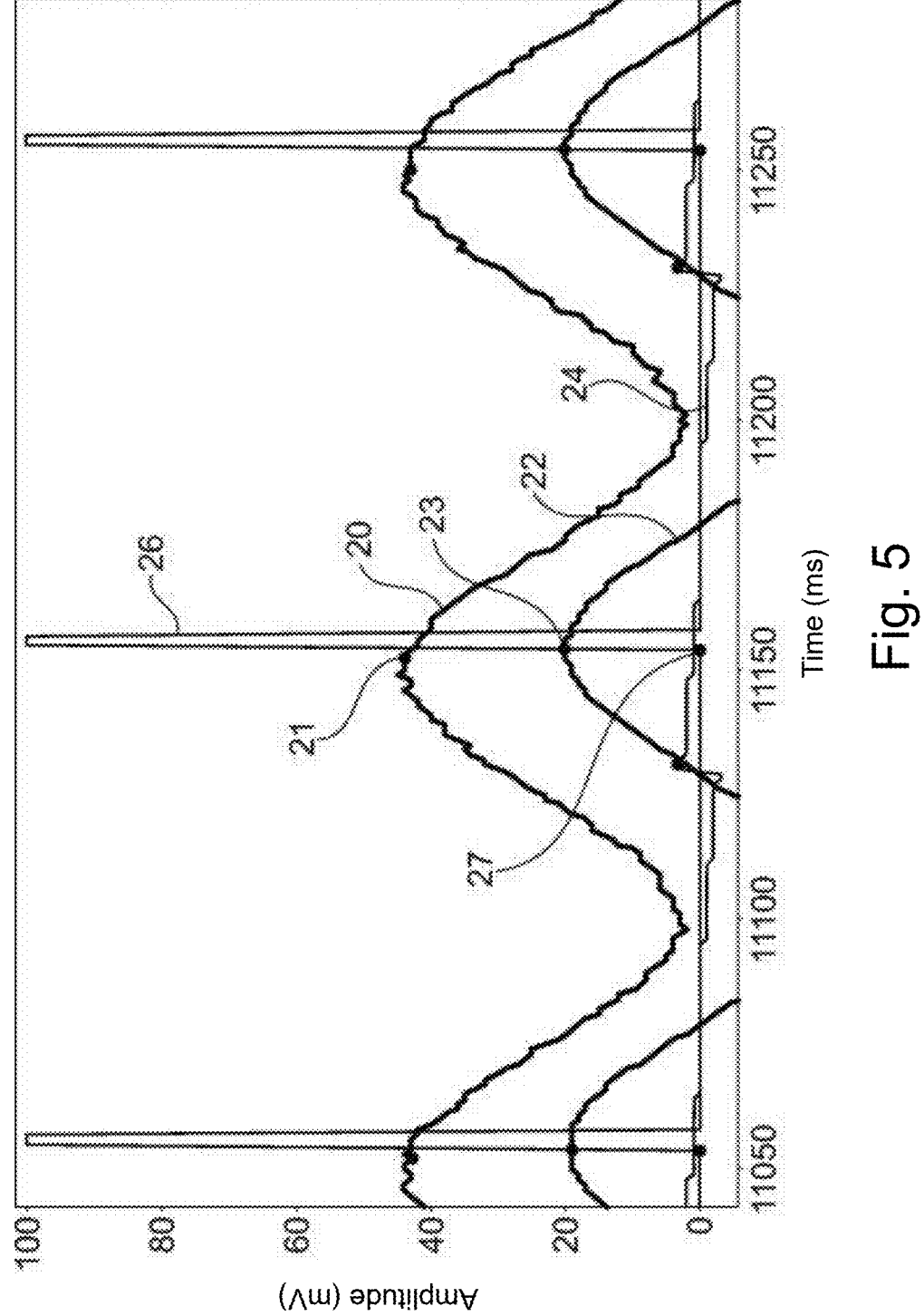
FIG. 5 shows a detection of an amplitude peak of a synthetic sinusoidal signal.
Figure 6:
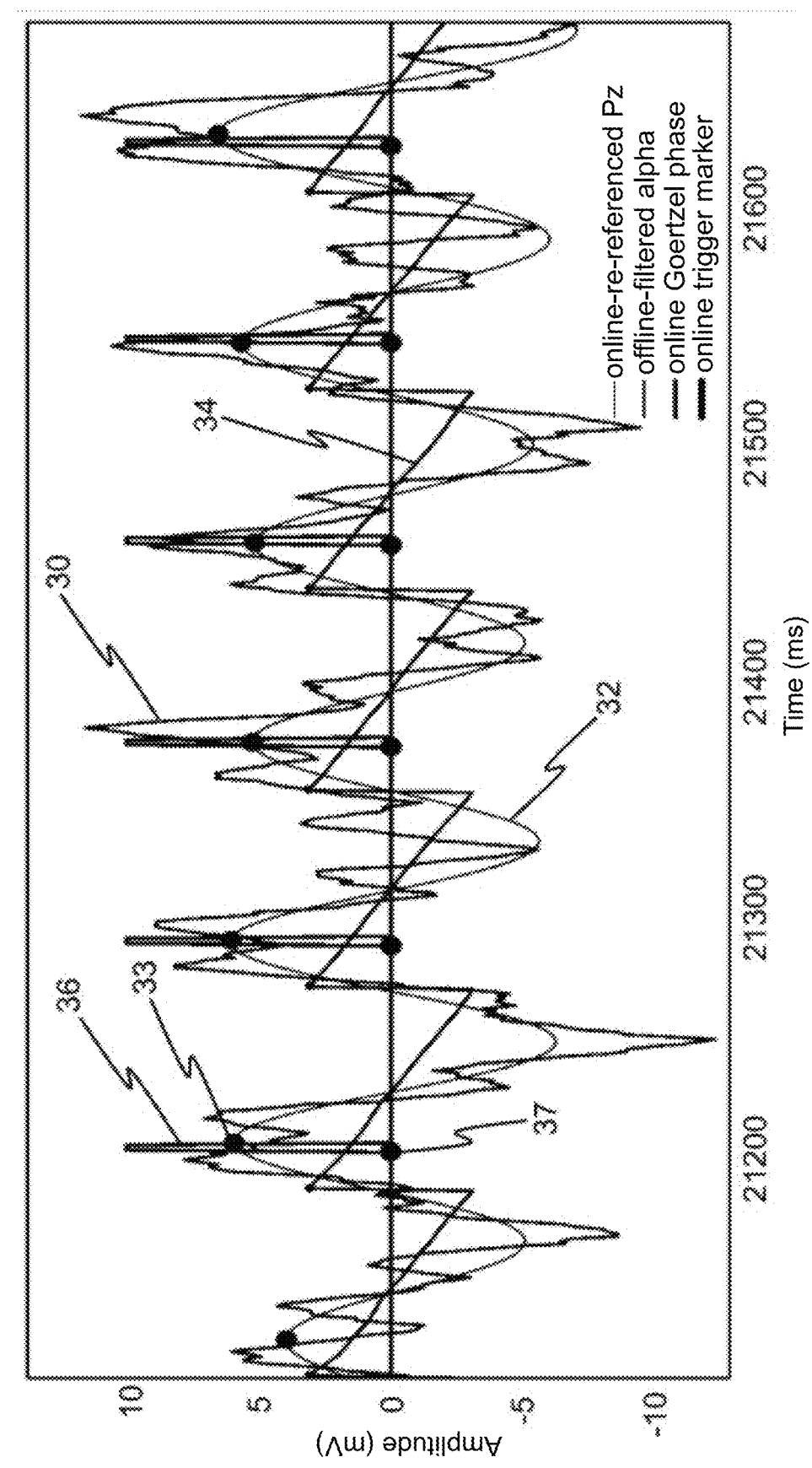
FIG. 6 shows a detection of the amplitude peak of an EEG signal.

The depictions of FIGS. 5 and 6 show measurements of a synthetic signal (FIG. 5) and an EEG signal (FIG. 6) during detection of the peak amplitude of the sinusoidal oscillation (phase:) 90°.

FIG. 5 shows the detection of the amplitude peak 21 of a synthetic sinusoidal signal 20 and the release of an event trigger 26. Here, the X axis shows the time in ms and the Y axis shows the amplitude of the signal in mV. The sinusoidal signal 20 is a signal measured by the assembly. At a phase of 90°, this signal 20 has a peak 21. For analysis and release of the trigger, the sinusoidal signal 20 is first converted to a filtered signal 22. The filtered signal 22 here is delayed with respect to the initial signal 20 by 1-2 ms, which is due to the processing time and the conversion of the original signal 20 to the filtered signal 22 within the measuring device. Accordingly, the filtered signal 22 has a peak 23, which occurs delayed by the same amount of time of 1-2 ms with respect to the actual peak 21 of the measuring signal 20. With the shown frequency of approx. 10 Hz, this time delay equals a phase of about 5°. When reaching the peak 23 determined in this way, a trigger signal 26 is released at this time 27. In the shown FIG. 5, this trigger signal 26 amounts to 100 mV. It is understood that in actual measurements of tissue, the voltage values are adjustable accordingly and can be adapted for measuring and/or stimulating tissue, for example. The graph 24 shown in FIG. 5 is the phase of this signal.

FIG. 6 shows the detection of an amplitude peak 33 of an actual EEG signal 30, referred to as online-re-referenced Pz in the figure legend, with sufficient signal-to-noise ratio. The graph 32 represents a sinusoidal signal calculated based on an offline signal filtering process—that is, one that might not meet real-time conditions. In order to meet real-time conditions, a phase signal 34 is generated by online-processing of the measuring signal 30, for example based on a Goertzel algorithm. The phase signal 34 here, also referred to as online Goertzel phase in the legend, always moves linearly from the phase of 0° to 360°. This movement allows determining the phase of 90°, and the trigger pulse is released at this time 37, as can be seen by the trigger signal 36 in FIG. 6.

According to the invention, the release of the event trigger may occur within 1 to 3 ms after reaching the actual peak of the measuring signal 30.

Due to application within the real-time environment, the measured result may be measured and evaluated quickly in this manner, so that no prediction for the future by the algorithm is required for stimulation. A simple Goertzel algorithm allows splitting up the spectral component, for example within the a-EEG band (8 to 12 Hz), calculating the phase in only two cycles and detecting the event (here: peak amplitude, phase) 90°.

Due to the very low jitter of the packet intervals, filter passing times may be considered in the calculation in order to generate even smaller consistent deviations.

The exemplary graphs shown herein were created without using the usual methods for prediction of the signal waveform. Signal prediction has been a common means in the prior art to release the trigger pulses in the correct phases. The real-time method according to the invention allows higher precision than is possible using prediction. It is conceivable, however, to continue using prediction for the methods provided according to the invention as well.

Figure 7:
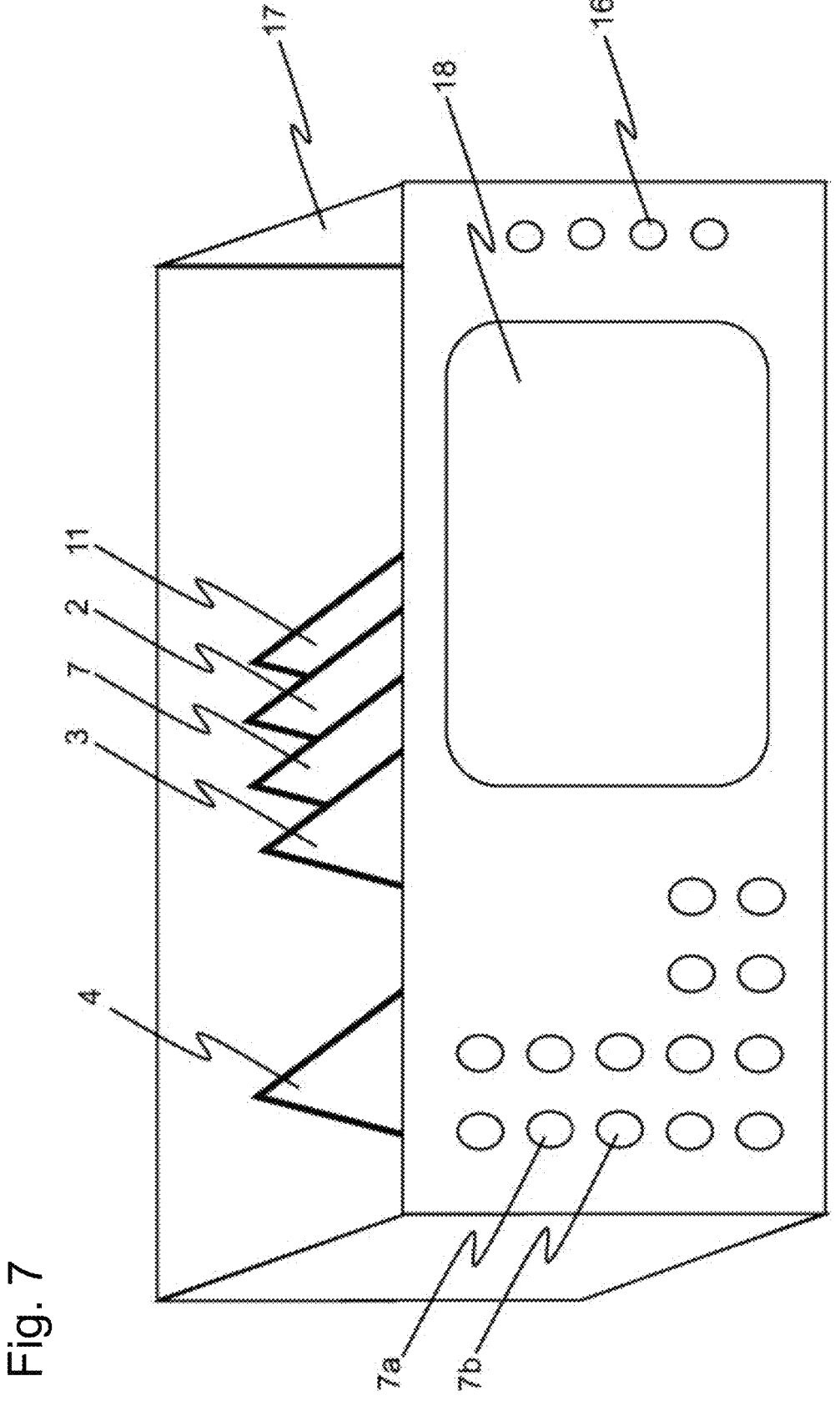
FIG. 7 shows an example of a device according to the invention having an integrated stimulation and measuring system.

FIG. 7 shows an example of a device having an integrated stimulation and measuring system. This device has a housing 17 including a master module 4 as well as a plurality of function modules 10, which are a capture module 3, a control module 7 and an action module 2 as well as a display module 10, for example a TFT module, in the given example. The function modules are connected by a BUS structure not visible here. A display device 18 is formed at a front of the housing 17. This display device 18 is connected to the display module 11. In this context, the display device 18 may have various functionalities as described above.

In addition, a series of ports 16 is provided at the front in the shown embodiment. Some of these ports are data inputs 7a and/or data outputs 7b of the control module 7. Other ports 16 are ports for other used function modules or for other functions in the device.

Further aspects of the invention are listed below:

Aspect 1: A method for body-condition-dependent stimulation with an action module 2 for stimulating tissue and a capture module 3 for deriving (measuring) bio data or bio signals and a signal processing module 4, which connects the action module 2 and the capture module 3, characterized in that the modules communicate via a protocol that meets hard or at least firm real-time requirements.

Aspect 2: The method for body-condition-dependent stimulation according to aspect 1, characterized in that the protocol is encapsulated within Ethernet frames.

Aspect 3: The method for body-condition-dependent stimulation according to aspect 2, characterized in that at least one of the modules 2, 3 already evaluates or edits data from a received Ethernet frame before the Ethernet frame is received by the module in its entirety.

Aspect 4: The method for body-condition-dependent stimulation according to aspect 3, characterized in that the module starts sending response data based on the evaluated or edited data before the Ethernet frame is received by the module in its entirety.

Aspect 5: The method for body-condition-dependent stimulation according to any one of the preceding aspects, characterized in that the modules communicate with one another in a closed loop and the data of the action module have effects on the behavior/function of the capture module and vice versa.

Aspect 6: The method for body-condition-dependent stimulation according to any one of the preceding aspects, characterized in that the stimulation is composed of neuromodulation excitation or inhibition.

Aspect 7: A system 1 for body-condition-dependent stimulation having an action module 2 for stimulating tissue and a capture module 3 for deriving (measuring) bio data or bio signals, characterized in that the two modules communicate via a communication link 5 that meets hard or at least firm real-time requirements.

Aspect 8: The system 1 for body-condition-dependent stimulation according to aspect 7, characterized in that the processing of at least part of a protocol stack of the communication link 5 is performed in hardware, e.g. by means of ASIC or FPGA.

Aspect 9: The system 1 for body-condition-dependent stimulation according to any one of aspects 7 and 8, characterized in that a bus protocol, protocol stack or hardware from the bus system EtherCAT is being used.

Aspect 10: The system 1 for body-condition-dependent stimulation according to any one of aspects 7 to 9, characterized in that a galvanic isolation 6 is provided between at least one module and the communication link 5.

Aspect 11: The system 1 for body-condition-dependent stimulation according to any one of aspects 7 to 10, characterized in that the bio data or bio signals are sent to the action module 2 and the action module 2 controls electric, magnetic, electromagnetic, mechanical, pneumatic and/or hydraulic actuators for directly influencing the biological tissue or organs while taking the bio data into account.

Aspect 12: The system 1 for body-condition-dependent stimulation according to any one of aspects 7 to 11, characterized in that the action module 2 performs multi-channel stimulation of biological tissue based on features from the bio data capture of bio signals of different origins by the capture module 3 in a frequency range of 0 to some kilohertz, in particular up to 100, 200 or 300 KHz.

Aspect 13: The system 1 for body-condition-dependent stimulation according to any one of aspects 7 to 12, characterized in that the action module 2 comprises a current pulse converter, the capture module 3 includes an EEG or ECG measuring unit and both modules are being plugged to a bus.

Aspect 14: The system 1 for body-condition-dependent stimulation according to any one of aspects 7 to 13, characterized in that apart from the action module 2 and the capture module 3, a signal processing module 4 is present, wherein a shared bus provides the communication links 5 between all modules, wherein the data measured by the capture module 3 is sent to the signal processing module 4 and processed, prepared and further processed by the same, and the signal processing module 4 sends data or commands to the action module 2 in order to activate stimulation.

Aspect 15: The system 1 for body-condition-dependent stimulation according to any one of aspects 6 to 14, characterized in that a processor-controlled module is a component of the bus, which monitors the system 1 and includes a communication interface to other computers connected via the Internet.

Aspect 16: The system 1 according to any one of aspects 14 or 15, characterized in that the signal processing module 3 is integrated within the action module 2 or the capture module 3.

Abbreviations

ECG-electrocardiogram
EEG-electroencephalogram
EMG-electromyogram
EOG-electrooculogram
ERG-electroretinogram
PPT-photoplethysmography
MCG-magnetocardiogram
MEG-magnetoencephalogram
BP 1 blood pressure
SpO2-oxygen saturation
RT-BUS real-time bus
USB-Universal Series Bus
LAN-Local Area Network
FES-functional electrical stimulation os-operating system
MIS-integrated stimulation and measuring system
TMS-transcranial magnetic stimulation
tES-transcranial electrical stimulation
nTMS-navigated transcranial magnetic stimulation
tDCS-transcranial direct current stimulation
tACS transcranial alternating current stimulation
tRNS transcranial random noise stimulation
DBS-deep brain stimulation
iAPF EEG alpha peak frequency
FES phase-related electrical peripheral stimulation

Reference Numerals

1 system for body-condition-dependent stimulation
2 action module/current module
3 capture module/EEG module
4 signal processing module/master module
5 communication link
6 galvanic isolation
7 control module
7*a* data input
7*b* data output
9 module slot
10 function module
11 display module, TFT module
12 control portion, RT-BUS interface
13 network module, LAN module
14 components, external devices
15 communication module, COM module
16 ports
17 housing
18 display
20 measuring signal
21 measuring signal peak
22 filtered signal
23 filtered signal peak
24 phase signal
26 trigger signal
27 trigger time
30 measuring signal
31 measuring signal peak
32 filtered signal
33 filtered signal peak
34 phase signal
36 trigger signal
37 trigger time.

The invention claimed is:

1. A system for body-condition-dependent stimulation, including a master module (4, Master) for processing module signals/data, a control module (7, DIQ module) for digital input/output control of actuators and at least two function modules, in particular an action module (2, D/A module) for stimulating tissue, and a capture module (3, A/D module) for deriving/measuring bio data or bio signals, characterized in that the communication between the modules takes place via a communication link (5) that meets hard or at least firm real-time requirements, the communication link (5) comprising a real-time-capable bus (ECAT) to which the at least two function modules are connected,
   the modules (2, 3, 4, 7) adapted to exchange information with one another on the real-time-capable bus (ECAT) during the same calculation step at a clock pulse provided by the master module (4, Master) depending on the data processing of the master module.

2. The system for body-condition-dependent stimulation according to claim 1, characterized in that the action module (2, D/A module) for actuating actuators for stimulating tissue, the capture module (3, A/D module) for deriving/measuring bio data or bio signals and the control module (7, DIO module) for digital input/output control of actuators, for stimulating tissue, of external devices are connected to the real-time-capable bus (ECAT).

3. The system for body-condition-dependent stimulation according to claim 1, characterized in that the capture module (3, A/D module) is designed to send the measured data/signals to the master module (4, Master) via the communication link (5), the master module (4, Master) is designed to process the received data and the master module (4, Master) is further designed to send data/commands to the action module (2, D/A module) to activate the stimulation of tissue via the actuators.

4. The system for body-condition-dependent stimulation according to claim 1, characterized in that the capture module (3, A/D module) comprises an A/D converter for converting analog bio data/bio signals captured by the capture module to digital signals to be processed in the master module (4, Master).

5. The system for body-condition-dependent stimulation according to claim 1, characterized in that the action module (2, D/A module) comprises a D/A converter for converting digital control signals provided by the master module (4, Master) to analog signals that are supplied to the actuators for stimulating tissue.

6. The system for body-condition-dependent stimulation according to claim 1, characterized in that the control module (7, DIO module) performs digital input/output control of the signal flow of digital control signals provided by the D/A converter of the action module (2, D/A module) and the master module (4, Master) by means of trigger signals (26, 36) generated by the master module (4, Master) and generated by the control module (DIO module).

7. The system for body-condition-dependent stimulation according to claim 1, characterized in that a galvanic isolation (6) is provided between at least one module (4, 7) and the real-time-capable bus (ECAT).

8. The system for body-condition-dependent stimulation according to claim 1, characterized in that the real-time-capable bus (ECAT) is an EtherCAT bus.

9. A method for body-condition-dependent stimulation based on the system according to claim 1, wherein the modules communicate with one another in a closed loop and the data of a function module, in particular an action module (2, D/A module), have effects on the behavior and/or function of a further function module, in particular a capture module (3, A/D module), and vice versa, wherein the master module (4, Master) generates a data packet at a predetermined clocking, in particular one data packet per millisecond, which is sent to the function modules to pass through them and returned to the master module via the communication link (5).

10. The method for body-condition-dependent stimulation according to claim 9, wherein an action module (2, D/A module) is provided, which receives and executes a control command for stimulation in the form of a neuromodulation excitation/inhibition.

11. The method for body-condition-dependent stimulation according to claim 9, wherein the action module (2, D/A module) controls magnetic, electromagnetic, mechanical, pneumatic and/or hydraulic actuators for directly influencing the biological tissue or organs.

12. The method for body-condition-dependent stimulation according to claim 9, wherein the action module (2, D/A module) performs multi-channel stimulation of biological tissue based on features from the bio data capture of bio signals of different origins by a capture module (3, A/D module) in a frequency range of 0 to some kilohertz, in particular up to 100, 200 or 300 kHz.

13. The method for body-condition-dependent stimulation according to claim 9, having a capture module (3, A/D module) designed to capture EEG, ECG, EXG, EMG, EOG, ERG, PPT, respiratory, MCG, MEG, BP, SpO2 signals.

* * * * *